United States Patent [19]
Olivier

[11] Patent Number: 5,080,103
[45] Date of Patent: Jan. 14, 1992

[54] SYRINGE FOR DOPPLER SONOGRAPHICALLY AIDED PENETRATION

[75] Inventor: Lucien C. Olivier, Essen, Fed. Rep. of Germany

[73] Assignee: Isotopen-Technik Dr. Sauerwein GmbH, Haan/Rheinl., Fed. Rep. of Germany

[21] Appl. No.: 496,890

[22] Filed: Mar. 21, 1990

[30] Foreign Application Priority Data

Mar. 21, 1989 [DE] Fed. Rep. of Germany ....... 3909140

[51] Int. Cl.⁵ .............................................. A61B 8/12
[52] U.S. Cl. .................... 128/662.05; 604/117
[58] Field of Search ................ 128/662.05, 662.06; 604/115–117

[56] References Cited

U.S. PATENT DOCUMENTS 3,556,079 1/1971 Omizo ............................. 128/24 A
4,887,606 12/1989 Yock et al. ................. 128/662.05

FOREIGN PATENT DOCUMENTS 0260953 9/1987 European Pat. Off. .
2142642 8/1971 Fed. Rep. of Germany .

OTHER PUBLICATIONS

EP 0190719 published Aug. 1986 "Blood Vessel Puncturing Device".

Primary Examiner—Francis Jaworski
Attorney, Agent, or Firm—Toren, McGeady & Associates

[57] ABSTRACT

In a syringe for ultrasonically aided penetration of arterial or venous vessels the transmitter and the receiver are arranged in the piston. This simplifies manipulation and, particularly if a physiological saline solution is simultaneously injected to directly couple the ultrasound to the soft parts surrounding the vessel, enables vessels even in anatomically difficult positions to be localized simply and without the danger of complications.

11 Claims, 2 Drawing Sheets

SYRINGE FOR DOPPLER SONOGRAPHICALLY AIDED PENETRATION

TECHNICAL FIELD OF THE INVENTION

The invention relates to the localisation and penetration of blood vessels, for example for injection or aspiration, and more particularly to a syringe having an ultrasonic receiver and a piston, and to a method of using them.

BACKGROUND OF THE INVENTION AND PRIOR ART

In intensive medicine, and also in many operating procedures, it is often necessary to introduce catheters into the large veins of the body to apply liquids and, for example, heart stimulating medication. Catheters are also introduced into the arterial vessel system, for example to the radial artery in the hand or the femoral artery in the groin to measure the blood pressure directly and to take blood to determine the amount of gas in the arterial oxygenated blood. Both arterial and venous catheter localisations are standard procedures not only in surgical clinics. Penetration of large vessels is also performed on numerous occasions in diagnostic procedures, for example special catheter examinations in angiography.

In particular the penetration of the subclavian vein beneath the collarbone and the penetration of the internal jugular vein on both sides of the neck is accompanied by a wide variety of complications, which are mainly caused by failed and repeated attempts at penetration. This can lead to so-called pneumothorax, injuries to the neck artery, haematoma formation and other serious iatrogenic injuries. When penetrating the radial artery or the femoral artery injuries to the vessels by multiple blind penetrations are possible even extending to an occlusion of the vessel concerned. Furthermore frustrated attempts at penetration lead to loss of time, which is most undesirable, for example, in the case of an emergency and even when preparing for an elective operation.

In order to avoid iatrogenic injuries when penetrating large veins it is known to determine the position and the course of the vessel to be penetrated sonographically. For example the image producing sonograph is used to localise the internal jugular vein of the neck. A great disadvantage of this practical method of avoiding iatrogenic injuries when penetrating large veins is, however, the outlay in apparatus. This has led to this simple and elegant method not being widely used, despite the extensive distribution of image producing sonographic devices.

To avoid difficulties when localising the vessel and to reduce the risk of complications it is also known to determine the position and the course of the vessel to be penetrated by means of ultrasonic Doppler sonography. This is done by means of a probe whose sonic head is aligned with the vessel to be penetrated and of an external receiver connected mechanically to a regular syringe. The receiver is arranged in the extension of the needle axis parallel to the housing of the syringe which is connected to the needle by way of a separate material line. The ultrasonic transmitter usually operates at a frequency of 4 to 8 MHz.

The ultrasonic waves are reflected by the blood corpuscles moving in the vessel and are thereby distorted due to the Doppler effect. The receiver receives the reflected ultrasonic waves and transmits via a loudspeaker a characteristic sound, which in the case of arteries is a pulse-synchronised hissing and in the case of veins is a respiration-dependent howling. Since the noise increases when approaching the vessel that is being sought ultrasonic Doppler sonography provides a simple means of localising vessels to determine the direction of the blood flow, since in the case of blood flowing towards the transmitter the ultrasonic waves are reflected at a higher frequency, and at a lower frequency in the case of blood flowing away from the transmitter.

There are however problems in manipulation since on the one hand the probe must be positioned, and independently thereof the needle of the syringe connected to the receiver must be introduced into the tissue. This usually requires an assistant to hold and position the probe, or at least occupies both hands of the examiner. Furthermore, the syringe connected to the receiver is a relatively complicated and scarcely compact special model which, as a result of its bulk and unfavourable centre of gravity can only be manipulated with difficulty. Emergency treatment is therefore not possible with syringes of this kind.

A further disadvantage common to both methods is that apart from the actual syringe the probe and—in Doppler sonography—the receiver have to be sterilised or be sterile-packed, which is not only troublesome but may also lead to damage to the electrical components.

OBJECT OF THE INVENTION

It is therefore an object of the invention to provide a syringe of simple construction which can be manipulated just like ordinary standard syringes for blind penetration.

SUMMARY OF THE INVENTION

To this end, according to the invention, in a syringe of the kind mentioned in the introduction the receiver, and preferably also the transmitter, is or are arranged in the piston. The arrangement of the transmitter in the piston of a regular syringe makes special positioning of the transmitter superfluous and ensures that the transmitter is always in an optimal position with regard to the vessel to be localised without an assistant or two hands being necessary. Just like the transmitter, the receiver can likewise also be arranged in the piston: this results in a particularly compact syringe which, if a loudspeaker is arranged in the piston, transmits the searching sound directly, or which may alternatively be coupled to an external loudspeaker by an induction coil arranged in the piston.

The piston can have a multi-part housing for simple assembly; it can be arranged in a sterile disposable sleeve and can thus be introduced into a regular syringe cylinder. In this way the system can be manipulated so that it is sterile and reliable while using regular syringe cylinders. Only the sterile disposable sleeve of the piston is thrown away after each use.

There is substantial simplification in localising the vessel being sought if, by means of the piston, after penetrating the skin and the subcutaneous fatty tissue, a small amount of a physiological saline solution in the syringe is injected to obtain direct coupling of the ultrasound to the soft parts surrounding the vessel being sought. In this way it is also possible to accurately locate and penetrate vessels located in deeper layers. As soon as the needle of the syringe has penetrated the vessel blood can be drawn out as in the case of blind vessel penetration and/or after removing the syringe according to the invention and its hollow needle from an indwelling cannula an intra-arterial or intravenous catheter can be applied in the usual manner. In contrast to the normal blind penetration technique the accurate positioning of the indwelling cannula can be checked by intermediate control of the Doppler signal. When it is difficult to push a catheter forward through such an indwelling cannula mispositioning of the cannula, which frequently causes problem in the application of vessel catheters, can thus be excluded.

The use of a plurality of quartz-stabilized transmitters and an equal number of quartz receivers ensures that during penetration a quartz pair always lies over the outlet opening for the penetration needle.

BRIEF DESCRIPTION OF THE DRAWINGS

The invention will now be described in more detail with reference to an exemplary embodiment shown in the drawings, in which.

DETAILED DESCRIPTION OF A PREFERRED EMBODIMENT OF THE INVENTION

Figure 1:
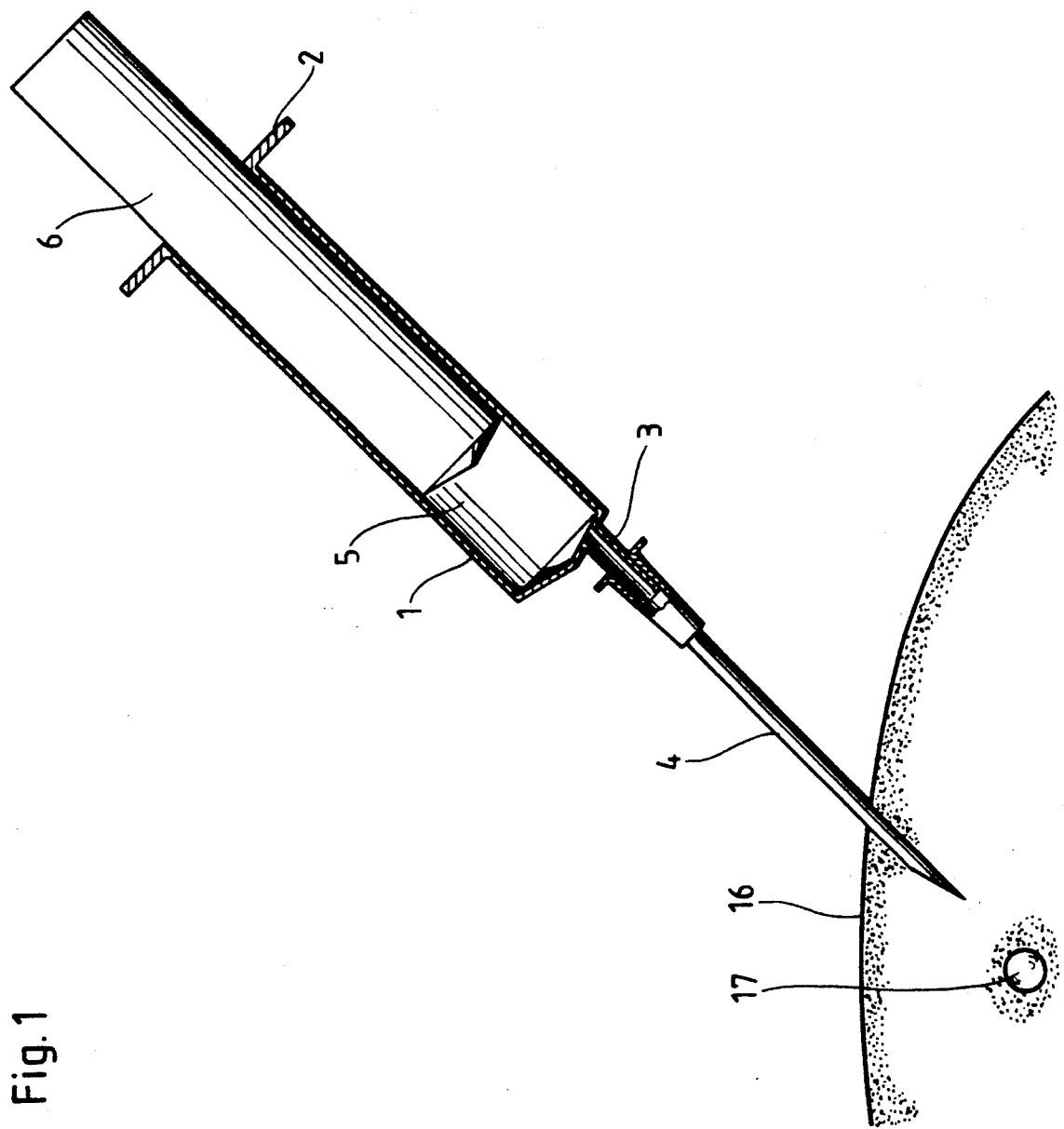
FIG. 1 shows a regular syringe with a Doppler sonographic piston in the course of localising a vessel.
Figure 2:
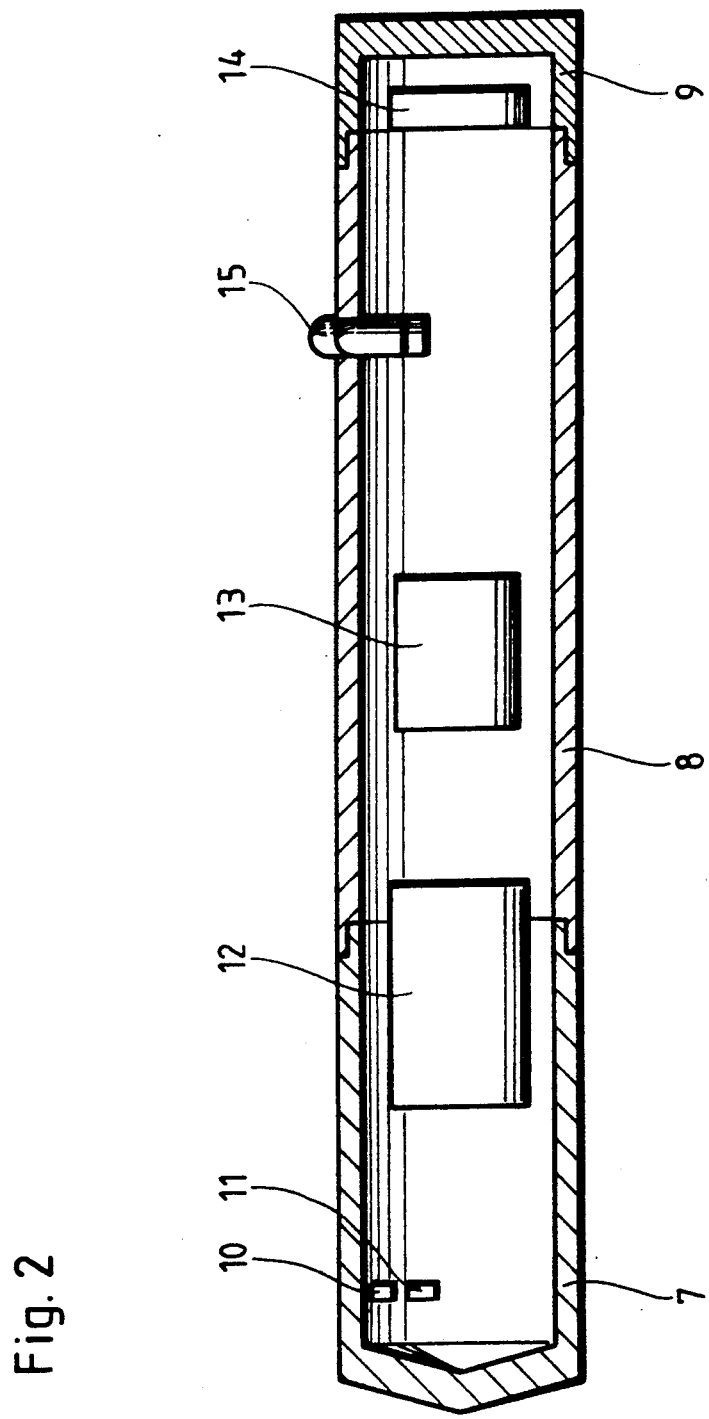
FIG. 2 shows a longitudinal section through the piston of the syringe shown in FIG. 1.

The syringe according to the invention comprises a regular syringe cylinder 1 with a purchase projection 2 and a base projection 3 to receive a penetration needle 4 or an indwelling cannula. In the interior 5 of the syringe there is a displaceable piston 6. This piston comprises a front part 7, a middle piece 8 and a cap 9. It contains in its front part 7 at least one quartz-stabilized transmitter 10 and an equal number of quartz receivers 11 which are connected to a transmitter/receiver circuit 12 by leads (not shown). A voltage source 13 that is preferably rechargeable serves as the current supply. Leads (not shown) extend from the circuit 12 to a loudspeaker 14 in the rear part of the piston. So that the transmitter 10 and the receiver do not have to be kept in operation permanently a momentary-contact switch 15 is arranged in the housing of the piston 6 which, when depressed, switches on the transmitter and at the same time also the receiver.

The needle 4 is guided through the skin 16 into the region of the vessel 17 to be localised. Then, by lightly pushing the piston 6 inwards a 9% saline solution present in the interior 5 of the syringe is injected to obtain improved propagation of the transcutaneous Doppler signal originating from the transmitter 10 and reflected by the vessel 17.

By means of the syringe according to the invention, even in the case of difficult anatomical topographic conditions and after failed blind penetration, vessels to be penetrated can be localised without difficulty and thereby mispenetration can be avoided reliably. The syringe according to the invention without the needle, or the piston alone, is also suitable as a probe for anatomical topographic investigation so as to first determine the course of the vessel and to determine the most advantageous approach path for the needle. With appropriately high ultrasonic intensity the syringe or the piston alone is also suitable for intraluminal and periluminal Doppler sonography.

What is claimed is:

1. A syringe for Doppler sonographically aided penetration of arterial and venous vessels, said syringe comprising a cylinder a receiver and a piston, said receiver is located in said piston, and said piston is cylinder, and adapted to inject fluid in cooperation therewith positioned within said syringe.

2. A syringe according to claim 1, wherein an ultrasonic transmitter is located in said piston.

3. A syringe according to claim 2, wherein at least one quartz-stabilized said transmitter and a corresponding number of quartz said receivers are located in said piston.

4. A syringe according to claim 1, wherein a loudspeaker is located in said piston.

5. A syringe according to claim 1, wherein said receiver is coupled inductively to an external loudspeaker by way of a coil located in said piston.

6. A syringe according to claim 1, wherein a momentary-contact switch is located in said piston.

7. A syringe according to claim 1, wherein the piston comprises a housing made up of a plurality of parts.

8. A piston unit for a syringe for Doppler sonographically aided penetration of arterial and venous vessels, comprising a piston adapted to cooperate with a syringe to inject fluid therefrom, and incorporating an ultrasonic receiver in said position receiver.

9. A piston unit according to claim 8, wherein said piston also incorporated an ultrasonic transmitter.

10. A syringe according to claim 9, which includes a sterile disposable for said piston.

11. A method of localising an arterial or venous vessel comprising the steps of inserting a syringe with a displaceable piston through a person's skin into the region of the vessel, transmitting ultrasonic waves from the piston towards the vessel, receiving reflected ultrasonic waves in the piston from the vessel, and during localisation injecting a physiological saline solution using said piston into the soft parts surrounding the vessel for obtaining direct coupling of the ultrasonic waves to the soft part surrounding the vessel.

* * * * *